United States Patent
Uber, III et al.

(10) Patent No.: US 11,013,857 B2
(45) Date of Patent: May 25, 2021

(54) CONTRAST HEATING SYSTEM WITH IN-LINE CONTRAST WARMER

(71) Applicant: BAYER HEALTHCARE LLC, Whippany, NJ (US)

(72) Inventors: Arthur E. Uber, III, Pittsburgh, PA (US); Molly Bingaman, McCandless, PA (US); Gerald Callan, Cranberry Township, PA (US); Kevin Cowan, Allison Park, PA (US); Genevieve Jerome, Pittsburgh, PA (US); Matthew Leroch, Pittsburgh, PA (US); Daniel Moore, Pittsburgh, PA (US); Ralph Schriver, Tarentum, PA (US); Michael Spohn, Fenelton, PA (US); Michael Swantner, Saxonburg, PA (US); Barry Tucker, Verona, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 146 days.

(21) Appl. No.: 16/314,897

(22) PCT Filed: Jul. 5, 2017

(86) PCT No.: PCT/US2017/040651
§ 371 (c)(1),
(2) Date: Jan. 3, 2019

(87) PCT Pub. No.: WO2018/009498
PCT Pub. Date: Jan. 11, 2018

(65) Prior Publication Data
US 2019/0307953 A1  Oct. 10, 2019

Related U.S. Application Data

(60) Provisional application No. 62/359,056, filed on Jul. 6, 2016.

(51) Int. Cl.
*A61M 5/145* (2006.01)
*A61M 5/44* (2006.01)

(52) U.S. Cl.
CPC .... *A61M 5/14546* (2013.01); *A61M 5/14566* (2013.01); *A61M 5/44* (2013.01);
(Continued)

(58) Field of Classification Search
CPC .... A61M 5/44; A61M 5/14546; A61M 5/007; A61M 5/445; A61M 2205/3368; A61M 2205/36; A61M 2205/127
See application file for complete search history.

(56) References Cited

U.S. PATENT DOCUMENTS 1,043,561 A   11/1912 Ayer
1,717,132 A   6/1929 Weinmann
(Continued)

FOREIGN PATENT DOCUMENTS

RU      40893 U1    10/2004
WO   9822168 A2     5/1998
(Continued)

OTHER PUBLICATIONS

Halsell; Robert D., "Heating Contrast Media in a Microwave Oven", Radiology, 1987, 163, 279-280.
(Continued)

*Primary Examiner* — Emily L Schmidt
(74) *Attorney, Agent, or Firm* — David Schramm; Joseph L. Kent; James R. Stevenson

(57) ABSTRACT

A system for heating a medical fluid has at least one first fluid container for storing the fluid, a fluid injector having at least one second fluid container for receiving the fluid from the at least one first fluid container through a fluid path set, at least one heating element positioned in-line with the fluid path set between the at least one first fluid container and the
(Continued)

at least one second fluid container of the fluid injector for heating the fluid to a pre-determined temperature as the fluid flows through at least one fluid path element, and a controller for controlling an output of the at least one heating element based on at least one of a property of the at least one heating element and a property of the fluid flowing through the at least one fluid path element.

15 Claims, 10 Drawing Sheets

(52) U.S. Cl.
CPC ............. *A61M 2005/14553* (2013.01); *A61M 2205/35* (2013.01)

(56) References Cited

U.S. PATENT DOCUMENTS

| | | |
|---|---|---|
| 1,987,119 A | 1/1935 | Long et al. |
| 2,388,111 A | 10/1945 | Berman et al. |
| 2,500,241 A | 3/1950 | Brown |
| 2,526,447 A | 10/1950 | Aiken |
| 3,485,245 A | 12/1969 | Lahr et al. |
| 3,607,134 A | 9/1971 | McIntyre |
| 3,807,467 A | 4/1974 | Tascher et al. |
| 4,038,519 A | 7/1977 | Foucras et al. |
| 4,167,663 A | 9/1979 | Granzow, Jr. et al. |
| 4,256,697 A | 3/1981 | Baldwin |
| 4,293,762 A | 10/1981 | Ogawa et al. |
| 4,464,563 A | 8/1984 | Jewett |
| 4,508,123 A | 4/1985 | Wyatt et al. |
| 4,532,414 A | 7/1985 | Shah et al. |
| 4,568,345 A | 2/1986 | Keilman et al. |
| 4,574,876 A | 3/1986 | Aid |
| 4,595,562 A | 6/1986 | Liston et al. |
| 4,628,186 A | 12/1986 | Bergemann et al. |
| 4,680,445 A | 7/1987 | Ogawa |
| 4,730,435 A | 3/1988 | Riddle et al. |
| 4,735,609 A | 4/1988 | Comeau et al. |
| 4,791,821 A | 12/1988 | Spencer |
| 4,842,028 A | 6/1989 | Kaufman et al. |
| 4,879,915 A | 11/1989 | Spencer |
| 4,906,816 A | 3/1990 | Van |
| 5,109,894 A | 5/1992 | McGregor |
| 5,125,069 A | 6/1992 | O'Boyle |
| 5,229,074 A | 7/1993 | Heath et al. |
| 5,254,094 A | 10/1993 | Starkey et al. |
| 5,295,964 A | 3/1994 | Gauthier |
| 5,370,674 A | 12/1994 | Farrell |
| 5,383,853 A | 1/1995 | Jung et al. |
| 5,408,576 A | 4/1995 | Bishop |
| 5,451,528 A | 9/1995 | Raymoure et al. |
| 5,479,969 A | 1/1996 | Hardie et al. |
| 5,502,944 A | 4/1996 | Kraft et al. |
| 5,522,512 A | 6/1996 | Archer et al. |
| 5,683,381 A | 11/1997 | Carr et al. |
| 5,690,614 A | 11/1997 | Carr et al. |
| 5,724,478 A | 3/1998 | Thweatt |
| 5,729,653 A | 3/1998 | Magliochetti et al. |
| 5,786,573 A | 7/1998 | Fabrikant et al. |
| 5,875,282 A | 2/1999 | Jordan et al. |
| 5,902,298 A | 5/1999 | Niedospial, Jr. et al. |
| 5,911,252 A | 6/1999 | Cassel |
| 5,921,419 A | 7/1999 | Niedospial, Jr. et al. |
| 5,928,197 A | 7/1999 | Niehoff |
| 5,935,523 A | 8/1999 | McCandless et al. |
| 5,968,014 A | 10/1999 | Neftel et al. |
| 5,989,238 A | 11/1999 | Ginsburg |
| 6,006,946 A | 12/1999 | Williams et al. |
| 6,035,102 A | 3/2000 | Bakke |
| 6,037,598 A | 3/2000 | Cicha |
| 6,047,108 A | 4/2000 | Sword et al. |
| 6,096,561 A | 8/2000 | Tayi |
| 6,139,528 A | 10/2000 | Kistner et al. |
| 6,142,974 A * | 11/2000 | Kistner ................. F28D 7/0091 604/113 |
| 6,146,359 A | 11/2000 | Carr et al. |
| 6,148,877 A | 11/2000 | Bethke |
| 6,261,261 B1 | 7/2001 | Gordon |
| 6,322,535 B1 | 11/2001 | Hitchins et al. |
| 6,360,794 B1 | 3/2002 | Turner |
| 6,375,624 B1 | 4/2002 | Uber, III et al. |
| 6,418,877 B1 | 7/2002 | Fredericks et al. |
| 6,436,349 B1 | 8/2002 | Carey et al. |
| 6,498,037 B1 | 12/2002 | Carey et al. |
| 6,512,212 B1 | 1/2003 | Leverne |
| 6,535,689 B2 | 3/2003 | Augustine et al. |
| 6,566,631 B2 | 5/2003 | Faries, Jr. et al. |
| 6,604,903 B2 | 8/2003 | Osborne et al. |
| 6,616,771 B2 | 9/2003 | Osborne et al. |
| 6,652,489 B2 | 11/2003 | Trocki et al. |
| 6,656,157 B1 | 12/2003 | Duchon et al. |
| 6,699,232 B2 | 3/2004 | Hart et al. |
| 6,722,782 B2 | 4/2004 | Faries, Jr. et al. |
| 6,824,528 B1 | 11/2004 | Faries, Jr. et al. |
| 6,877,530 B2 | 4/2005 | Osborne et al. |
| 7,017,623 B2 | 3/2006 | Tribble et al. |
| 7,031,602 B2 | 4/2006 | Faries, Jr. et al. |
| 7,128,105 B2 | 10/2006 | Tribble et al. |
| 7,240,699 B2 | 7/2007 | Osborne et al. |
| 7,357,786 B1 | 4/2008 | Bakke |
| 7,394,976 B2 | 7/2008 | Entenman et al. |
| 7,540,864 B2 | 6/2009 | Faries, Jr. et al. |
| 7,553,294 B2 | 6/2009 | Lazzaro et al. |
| 7,610,115 B2 | 10/2009 | Rob et al. |
| 7,618,397 B2 | 11/2009 | Hicks |
| 7,662,124 B2 | 2/2010 | Duchon et al. |
| 7,666,169 B2 | 2/2010 | Cowan et al. |
| 7,728,711 B2 | 6/2010 | Shoenfeld |
| 7,814,731 B2 | 10/2010 | Bender et al. |
| 7,900,658 B2 | 3/2011 | Osborne et al. |
| 7,931,859 B2 | 4/2011 | Mlodzinski et al. |
| 7,942,851 B2 | 5/2011 | Faries, Jr. et al. |
| 7,988,666 B2 | 8/2011 | Zhang et al. |
| 8,141,598 B2 | 3/2012 | Fago et al. |
| 8,226,293 B2 | 7/2012 | Faries, Jr. et al. |
| 8,226,605 B2 | 7/2012 | Faries, Jr. et al. |
| 8,267,129 B2 | 9/2012 | Doherty et al. |
| 8,286,671 B1 | 10/2012 | Strangis |
| 8,317,099 B2 | 11/2012 | Perkins et al. |
| 8,386,070 B2 | 2/2013 | Eliuk et al. |
| 8,403,880 B2 | 3/2013 | Hopping et al. |
| 8,463,362 B2 | 6/2013 | Fago |
| 8,467,671 B2 | 6/2013 | French et al. |
| 8,539,989 B2 | 9/2013 | Giribona et al. |
| 8,580,574 B2 | 11/2013 | Smith |
| 8,692,167 B2 | 4/2014 | Hedmann et al. |
| 8,803,044 B2 | 8/2014 | Kienman et al. |
| 8,807,177 B2 | 8/2014 | Strangis |
| 8,821,011 B2 | 9/2014 | Faries, Jr. et al. |
| 8,920,387 B2 | 12/2014 | Faries, Jr. et al. |
| 8,924,036 B2 | 12/2014 | McKinnon |
| 8,948,581 B2 | 2/2015 | French et al. |
| 9,119,912 B2 | 9/2015 | Faries, Jr. et al. |
| 9,173,995 B1 | 11/2015 | Tucker et al. |
| 9,199,033 B1 | 12/2015 | Cowan et al. |
| 9,474,857 B2 | 10/2016 | Riley et al. |
| 2002/0081109 A1 | 6/2002 | Mitsunaga et al. |
| 2003/0028144 A1 | 2/2003 | Duchon et al. |
| 2003/0135252 A1* | 7/2003 | MacHold ............. A61F 7/0085 607/106 |
| 2003/0216692 A1* | 11/2003 | Fago ................... A61M 31/005 604/150 |
| 2003/0229309 A1 | 12/2003 | Babkes et al. |
| 2004/0199075 A1 | 10/2004 | Evans et al. |
| 2005/0045242 A1 | 3/2005 | Osborne |
| 2005/0119604 A1 | 6/2005 | Bonney et al. |
| 2005/0137524 A1 | 6/2005 | Sakal et al. |
| 2005/0203329 A1 | 9/2005 | Muto et al. |
| 2005/0224137 A1 | 10/2005 | Tribble et al. |
| 2005/0252574 A1 | 11/2005 | Khan et al. |
| 2005/0278066 A1 | 12/2005 | Graves et al. |

(56) References Cited

U.S. PATENT DOCUMENTS

| | | |
|---|---|---|
| 2006/0030917 A1 | 2/2006 | Eccleston et al. |
| 2006/0081305 A1 | 4/2006 | Monti |
| 2006/0271014 A1 | 11/2006 | Hynes et al. |
| 2007/0045272 A1 | 3/2007 | French et al. |
| 2007/0110637 A1 | 5/2007 | Phelps |
| 2007/0140925 A1 | 6/2007 | Phelps |
| 2007/0225601 A1 | 9/2007 | Uber, III et al. |
| 2008/0004576 A1 | 1/2008 | Tanaka et al. |
| 2008/0021164 A1 | 1/2008 | Masuda et al. |
| 2008/0081000 A1 | 4/2008 | MacLeod et al. |
| 2008/0114328 A1 | 5/2008 | Doherty et al. |
| 2008/0147014 A1 | 6/2008 | Lafferty |
| 2008/0188808 A1 | 8/2008 | Hynes et al. |
| 2008/0211674 A1 | 9/2008 | Gibson et al. |
| 2009/0012655 A1 | 1/2009 | Kienman et al. |
| 2009/0198208 A1 | 8/2009 | Stavsky et al. |
| 2009/0280572 A1 | 11/2009 | Ribeiro et al. |
| 2009/0281460 A1 | 11/2009 | Lowery et al. |
| 2009/0319011 A1 | 12/2009 | Rosiello |
| 2010/0217154 A1 | 8/2010 | Deshmukh et al. |
| 2011/0046551 A1 | 2/2011 | Augustine et al. |
| 2011/0202034 A1 | 8/2011 | Lopez |
| 2011/0307117 A1 | 12/2011 | McKinnon et al. |
| 2012/0053457 A1* | 3/2012 | Fago ................... A61M 39/10 600/432 |
| 2012/0330152 A1 | 12/2012 | Reisinger et al. |
| 2013/0165848 A1 | 6/2013 | Sebesta et al. |
| 2013/0340795 A1 | 12/2013 | Gaskill-Fox et al. |
| 2014/0094883 A1 | 4/2014 | Lim et al. |
| 2014/0199057 A1 | 7/2014 | Hansen et al. |
| 2014/0224784 A1 | 8/2014 | Kohler |
| 2015/0359976 A1 | 12/2015 | Richards |
| 2016/0213829 A1 | 7/2016 | Klewinghaus |

FOREIGN PATENT DOCUMENTS

| | | |
|---|---|---|
| WO | 9910027 A1 | 3/1999 |
| WO | 2004091688 A2 | 10/2004 |
| WO | 2006083359 A2 | 8/2006 |
| WO | 2006108026 A2 | 10/2006 |
| WO | 2007021746 A2 | 2/2007 |
| WO | 2007033103 A1 | 3/2007 |
| WO | 2008076631 A2 | 6/2008 |
| WO | 2015164783 A1 | 10/2015 |
| WO | 2016112163 A1 | 7/2016 |
| WO | 2016191485 A1 | 12/2016 |

OTHER PUBLICATIONS

Halsell; Robert D., "Heating Contrast Media: Role in Contemporary Angiography", Radiology, Jul. 1987, 276-278.

"International Preliminary Report on Patentability and Written Opinion from PCT Application No. PCT/US2017/040651", dated Jan. 17, 2019.

Schwab Siegfried A. et al., "Peripheral Intravenous Power Injection of Iodinated Contrast Media: The Impact of Temperature on Maximum Injection Pressures at Different cannula Sizes", Acad Radiol, 2009, 16, 1502-1508.

Watlow., "Thermal Solutions for Medical and Clinical Applications", 2012.

"Brochure for 3M Ranger Blood/Fluid Warming System With Smartheat Technology", 3M Health Care Limited, Mar. 2011.

Dre; Veterinary., "Medi-Temp III Blood/Fluid Warming Unit Website", website accessed Feb. 19, 2015.

"Freeflex Heated Tubing Product", Watlow, website accessed Feb. 16, 2015.

Grollman Jr.; J.H., "The Importance of Preheating Contrast Media", American Roentgen Ray Society, Feb. 1984, 142, 391-392.

"Standard Specification for Blood/Intravenous Fluid/Irrigation Fluid Warmers", ASTM International, accessed Apr. 9, 2015, p. 1-20.

* cited by examiner

CONTRAST HEATING SYSTEM WITH IN-LINE CONTRAST WARMER

CROSS-REFERENCE TO RELATED APPLICATIONS

This application is a 371 national phase application of PCT International Application No. PCT/US2017/040651, filed Jul. 5, 2017, and claims the priority to U.S. Provisional Patent Application No. 62/359,056, filed on Jul. 6, 2016, the disclosures of which are incorporated herein by reference in their entirety.

BACKGROUND OF THE DISCLOSURE

Field of the Disclosure

The present disclosure relates generally to a system for delivering fluid to a patient and, in particular, relates to a fluid injection system having a heating system for heating the fluid prior to delivering the fluid to a patient.

Description of Related Art

In many medical diagnostic and therapeutic procedures, a medical practitioner, such as a physician, injects a patient with one or more medical fluids. In recent years, a number of injector-actuated syringes and fluid injectors for pressurized injection of fluids, such as imaging contrast solutions (often referred to simply as "contrast"), flushing agents, such as saline, and other medical fluids have been developed for use in procedures such as angiography, computed tomography (CT), ultrasound, magnetic resonance imaging (MRI), nuclear medicine, positron emission tomography (PET), and other imaging procedures. In general, these fluid injectors are designed to deliver a preset amount of fluid at a preset flow rate.

It is sometimes desirable to heat the contrast before or during the injection procedure. Heating the contrast to a temperature above room temperature and at or below normal body temperature (for example, approximately 37° C.) decreases its viscosity and allows for injections at a higher flow rate with a lower pressure compared to injections performed with room-temperature contrast. In addition, patient comfort is increased during the injection procedure when using the heated contrast. In some examples, a contrast container, such as a bottle, syringe, or a vial, is stored in a warmer. The heated contrast is then removed from the warmer and loaded onto the fluid injector before performing the injection procedure. In other examples, a contrast heater is positioned within the fluid line between the fluid injector and the patient such that the room-temperature contrast delivered by the fluid injector is heated as it is injected into the patient.

Some of the conventional contrast warmers require separate equipment that may be bulky and may take up valuable space in the imaging suite. In addition to meet a heavy imaging schedule, large amounts of contrast must be pre-heated ahead of time, which can require additional warming capability and planning. Further, certain regulatory requirements, such as those under the Joint Commission: Accreditation, Health Care, Certification (JCAHO) in the United States, may impose rules regarding contrast heating that may be burdensome to satisfy in practice. For example, some rules may require that the temperature of the contrast cannot be maintained once the contrast container is taken out of the contrast warmer and loaded onto the fluid injector. To overcome this, some injectors have a contrast heat maintainer which users need to place on the syringe, but the heat maintainers are not sufficient to heat cold contrast in a reasonable time. Other contrast warmers do not allow contrast to be sufficiently heated prior to being injected by the fluid injector. In this manner, insufficient flow rates may result from injections using the high-viscosity, room-temperature contrast due to being limited to a maximum pressure for the given contrast at a given temperature. Accordingly, there is a need in the art for an improved contrast heating system.

SUMMARY OF DISCLOSURE

In view of the disadvantages of the existing techniques for heating contrast before it is delivered to a patient, there is a need in the art for an improved contrast heating system configured for heating contrast as it is delivered from a single patient container or bulk fluid container (a first fluid container) to an intermediate or second fluid container (e.g., a syringe, pump, bag, tubing set or other fluid path element or elements containing a significant volume of fluid), and/or a fluid injector system [e.g. a peristaltic pump], and prior to being delivered to a patient.

In accordance with some examples, a system for heating a medical fluid may comprise at least one first fluid container for storing the fluid, a fluid injector having at least a second fluid container, such as at least one syringe, for receiving the fluid from the first fluid container through a fluid path set, at least one heating element positioned in-line with the fluid path set between the at least one first fluid container and the at least one second fluid container of the fluid injector for heating the fluid to a pre-determined temperature as the fluid flows through at least one cartridge or fluid path element of the at least one heating element, and a controller for controlling an output of the at least one heating element based on at least one of a property of the at least one heating element and a property of the fluid flowing through the at least one fluid path element or cartridge. The property of the fluid may comprise flow rate, total volume, heat capacity, temperature, viscosity, or any combination thereof. The property of the at least one heating element may be a temperature, electrical resistivity, thermal transfer resistivity, thermal mass, heat capacity, or heat input of the at least one heating element.

In accordance with other examples, the at least one fluid path element or cartridge may comprise at least one fluid conduit having a first end in fluid communication with a first portion of the fluid path set connected to the at least one first fluid container and a second end in fluid communication with a second portion of the fluid path set connected to the at least one second fluid container. The at least one fluid conduit of the at least one fluid path element or cartridge may have a serpentine path. The at least one fluid path element or cartridge may be removably connected to the first portion and the second portion of the fluid path set with one or more connectors. The at least one fluid path element or cartridge may be monolithically formed with or permanently connected to the first portion and the second portion of the fluid path set. The fluid path set may be removably inserted into a tubing pathway of the at least one fluid path element or cartridge. The at least one heating element may comprise at least a pair of heating elements provided on opposing sides or surfaces of the at least one fluid path element or cartridge. The at least one heating element may comprise a plurality of heating elements arranged in series along a longitudinal length of the at least one fluid path element or cartridge, for example on opposing sides or surfaces or on one side or surface of the at least one fluid path element or cartridge. The at least one heating element may be a plurality of heating elements arranged in parallel. The plurality of heating elements may be energized separately or uniformly by the controller, for example so that the heating elements may be at the same or different temperatures. The at least one heating element may heat the fluid from the first fluid container to a temperature between about 35° C. and about 41° C. as it flows over, through, or otherwise contacts the at least one heating element.

In accordance with other examples, the system may have at least one sensor, for example a temperature sensor, for measuring a temperature or flow rate of the fluid flowing through the at least one fluid path element or cartridge. The at least one sensor may be positioned at least one of an inlet of at least one fluid conduit of the at least one fluid path element or cartridge, an outlet of the at least one fluid conduit of the at least one fluid path element or cartridge, and/or any location between the inlet and the outlet of the at least one fluid conduit of the at least one fluid path element or cartridge. The at least one sensor may comprise at least one temperature sensor that may optionally measure the temperature of the fluid in the first fluid container and/or in the second fluid container. The at least one temperature sensor may be a contact thermometer, an infrared thermometer, a thermochromic ink label or marking, or a phase change indicator. The controller may receive data from the at least one sensor, for example temperature data from the at least one temperature sensor, and transmit the data to the fluid injector via a wired or wireless connection to the fluid injector, processor, or other information network, for example a hospital information network. The fluid injector may be configured to modify a pre-programmed injection protocol based at least in part on data received from the controller. The fluid injector may adjust an injection pressure limit based on the temperature of the fluid or the flow rate of the fluid. The fluid injector may inform the operator of the fluid temperature and/or the expected viscosity. A heat maintainer may be provided for maintaining a temperature of the heated fluid while it is in the second fluid container. The heat maintainer may be a sleeve, such as an insulated sleeve or heated sleeve, surrounding at least a portion of at least one second fluid container.

In accordance with other examples, a system for heating a medical fluid may comprise at least one first fluid container for storing the fluid, a fluid injector comprising at least one pump for delivering the fluid from the at least one first fluid container to a patient through a fluid path set, at least one heating element positioned between the at least one first fluid container and the at least one pump of the fluid injector for heating the fluid to a pre-determined temperature, and a controller for controlling an output of the at least one heating element based, for example on a flow rate of the fluid through the fluid path set and/or a contact time of the contrast with the at least one heating element. The pump may be a peristaltic pump, a piston pump, or a syringe. The system may further have at least one sensor, for example, at least one temperature sensor for measuring a temperature of the fluid flowing through the fluid path set or at least one flow rate sensor for measuring the flow rate of the fluid flowing through the fluid path. The at least one sensor may be positioned at at least one of an inlet of the fluid path set, an outlet of the fluid path set, and/or any location between the inlet and the outlet of the fluid path set. The at least one sensor may optionally measure the temperature of the fluid in the first fluid container before it enters the fluid path or after it leaves the pump.

Various other aspects of the present disclosure are recited in one or more of the following clauses:

Clause 1. A system for heating a medical fluid, the system comprising: at least one first fluid container for storing the fluid; a fluid injector having at least one second fluid container for receiving the fluid from the at least one first fluid container through a fluid path set; at least one fluid path element positioned in-line with at least a segment of the fluid path set between the at least one first fluid container and the at least one second fluid container of the fluid injector for heating the fluid to a pre-determined temperature as the fluid flows through the at least one fluid path element; and a controller for controlling an output of the at least one fluid path element based on at least one of a property of the fluid path element and a property of the fluid flowing through the at least one fluid path element.

Clause 2. The system of clause 1, wherein the at least one fluid path element has at least one fluid conduit having a first end in fluid communication with a first portion of the fluid path set connected to the first fluid container and a second end in fluid communication with a second portion of the fluid path set connected to the at least one second fluid container.

Clause 3. The system of clause 2, wherein the at least one fluid conduit of the at least one fluid path element has a serpentine path.

Clause 4. The system of any one of clauses 1-3, wherein the at least one fluid path element is removably connected to the fluid path set with one or more connectors or by placing the fluid path set within a tubing pathway of the fluid path element.

Clause 5. The system of any one of clauses 1-4, wherein the at least one fluid path element is monolithically formed with the fluid path set.

Clause 6. The system of any one of clauses 1-5, wherein the at least one fluid path element comprises a pair of heating elements provided on opposing sides of the at least one fluid path element.

Clause 7. The system of any one of clauses 1-6, wherein the at least one fluid path element comprises a plurality of heating elements arranged in series along a longitudinal length of the at least one fluid path element.

Clause 8. The system of any one of clauses 1-7, wherein the at least one heating element comprises a plurality of heating elements arranged in parallel along a length of the at least one fluid path element.

Clause 9. The system of any one of clauses 1-8, further comprising at least one temperature sensor for measuring a temperature of the fluid flowing through at least a portion of the at least one fluid path element.

Clause 10. The system of clause 9, wherein the at least one temperature sensor is positioned at at least one of an inlet of at least one fluid conduit of the at least one fluid path element, an outlet of the at least one fluid conduit of the at least one fluid path element, and any location between the inlet and the outlet of the at least one fluid conduit of the at least one fluid path element.

Clause 11. The system of clause 9 or clause 10, wherein the at least one temperature sensor is a contact thermometer, an infrared thermometer, a thermochromic ink label or marking, a phase change indicator or combination of any thereof.

Clause 12. The system of any one of clauses 9-11, wherein the controller receives temperature data from the at least one temperature sensor and transmits the temperature data to the fluid injector via a wired or wireless connection.

Clause 13. The system of clause 12, wherein the fluid injector is configured to modify a pre-programmed injection protocol based in part on temperature data received from the controller.

Clause 14. The system of clause 12 or clause 13, wherein the fluid injector adjusts an injection pressure limit based in part on the temperature of the fluid.

Clause 15. The system of any one of clauses 1-14, further comprising a heat maintainer associated with the at least one second fluid container for maintaining a temperature of the heated fluid.

Clause 16. The system of any one of clauses 1-5, wherein the heat maintainer comprises a sleeve surrounding at least a portion of the at least one second fluid container.

Clause 17. A system for heating a medical fluid, the system comprising: at least one first fluid container for storing the fluid; a fluid injector having at least one pump for delivering the fluid from the at least one first fluid container to a patient through a fluid path set; at least one fluid path element positioned between the at least one first fluid container and the at least one pump of the fluid injector for heating the fluid to a pre-determined temperature; and a controller for controlling an output of the at least one fluid path element based on at least one of a property of the fluid path element and a property of the fluid flowing through the fluid path set.

Clause 18. The system of clause 17, wherein the at least one pump comprises a peristaltic pump or at least one syringe.

Clause 19. The system of clause 17 or 18, further comprising at least one temperature sensor for measuring a temperature of the fluid flowing through the fluid path set.

Clause 20. The system of clause 18, wherein the at least one temperature sensor is positioned at at least one of an inlet of the fluid path set, an outlet of the fluid path set, and/or any location between the inlet and the outlet of the fluid path set.

These and other features and characteristics of the contrast heating system, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in various figures. It is to be expressly understood, however, that the drawings are for the purpose of illustration and description only.

DETAILED DESCRIPTION

Figure 1:
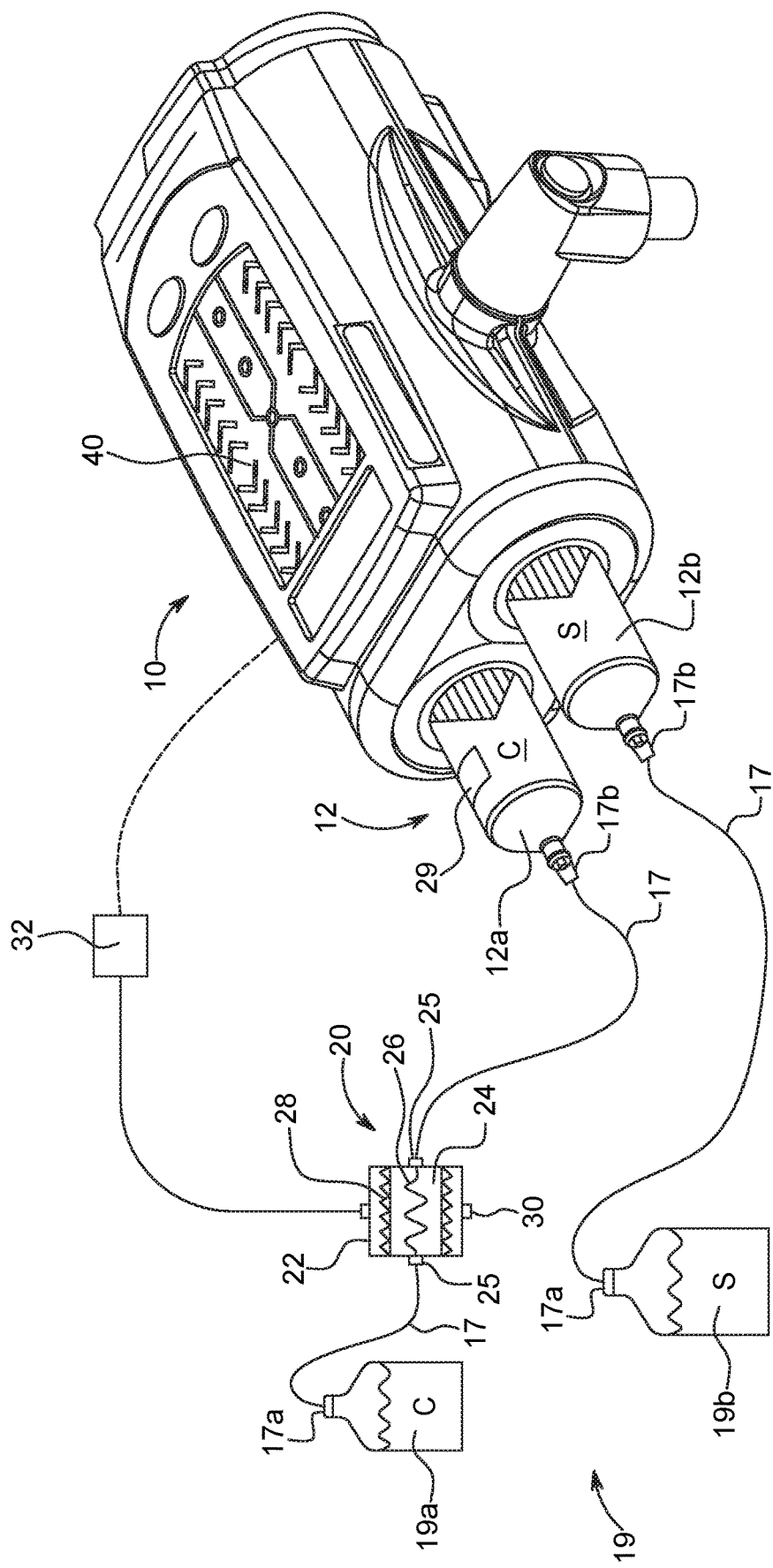
FIG. 1 is a top perspective view of a system including a fluid injector and a heating system according to one aspect of the present disclosure.

The illustrations generally show preferred and non-limiting aspects of the systems and methods of the present disclosure. While the description presents various aspects of the devices and components thereof, it should not be interpreted in any way as limiting the disclosure. Furthermore, modifications, concepts, and applications of the disclosure's aspects are to be interpreted by those skilled in the art as being encompassed, but not limited to, the illustrations and descriptions herein.

The following description is provided to enable those skilled in the art to make and use the described aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure.

For purposes of the description hereinafter, the terms "upper," "lower," "right," "left," "vertical," "horizontal," "top," "bottom," "lateral," "longitudinal," and derivatives thereof shall relate to the disclosure as it is oriented in the drawing figures. The term "proximal," when used with reference to any component of a contrast heating system, refers to a portion of a component of a contrast heating system that is nearest to an injector and/or a fluid source and furthest from a patient. The term "distal," when used with reference to any component of a contrast heating system, refers to a portion of a component of a contrast heating system that is furthest from an injector and/or a fluid source and nearest to a patient. It is also to be understood that the specific devices and processes illustrated in the attached drawings, and described in the following specification, are simply exemplary aspects of the disclosure. Hence, specific dimensions and other physical characteristics related to the aspects (i.e., aspects, variants, variations) disclosed herein are not to be considered limiting.

Referring to the drawings in which like reference characters refer to like parts throughout the several views thereof, the present disclosure is generally directed to a contrast heating system. Various aspects of the present disclosure provide a contrast heating system configured for use with a fluid injector for delivering heated contrast to a patient.

With reference to FIG. 1, a fluid injector 10 (hereinafter referred to as "injector 10"), such as an automated or powered fluid injector, is adapted to interface with and actuate at least one syringe 12, such as a first syringe 12a and a second syringe 12b. Each of the at least one syringe 12 may be independently filled with a medical fluid. For example, the first syringe 12a may be filled with a first fluid, such as contrast agent C or any desired first medical fluid, while the second syringe 12b may be filled with a second fluid, such as saline solution S or any second desired medical fluid. The injector 10 may be used during a medical procedure to inject the medical fluid into the body of a patient by driving a plunger of at least one syringe 12 with at least one piston. The injector 10 may be a multi-syringe injector, wherein several syringes 12 may be oriented in a side-by-side or other arrangement and include plungers separately actuated by respective pistons associated with the injector 10. In examples with two syringes 12a, 12b arranged in a side-by-side relationship and filled with two different medical fluids, the injector 10 may deliver fluid from one or both of the syringes 12 simultaneously or sequentially. In another embodiment, the injector 10 may comprise three syringes in a side-by-side arrangement.

Examples of suitable front-loading fluid injectors 10 that may be used or modified for use with the contrast heating system are disclosed in U.S. Pat. Nos. 5,383,858; 7,553,294; 7,666,169; 9,173,995; 9,199,033; and 9,474,857; and in International Patent Application Publication Nos. WO 2015/164783; WO 2016/112163; and WO 2016/191485, the disclosures of which are incorporated by reference in their entirety.

Exemplary syringes 12 suitable for use with the injector 10 depicted in FIG. 1 are described in U.S. Pat. Nos. 5,383,858; 6,322,535; 6,652,489; 9,173,995; and 9,199,033; and in International Patent Application Publication Nos. WO 2015/164783; WO 2016/112163; and WO 2016/191485, the disclosures of which are all incorporated by reference in their entireties.

With continued reference to FIG. 1, at least one fluid path set 17 may be fluidly connected with the at least one second fluid container, such as a syringe 12, for delivering the fluid from the at least one syringe 12 to a catheter, needle, or other fluid delivery device (not shown) inserted into a patient at a vascular access site. The at least one fluid path set 17 may also be used for filling the at least one second fluid container, for example syringe 12, with fluid from at least one first fluid container 19, such as shown in FIG. 1. The fluid path set 17 may be configured as tubing having an interior lumen for delivering fluid therethrough. The fluid path set 17 desirably has a first connector 17a for connecting a first end of a first portion of the fluid path set 17 to the at least one first fluid container 19 and a second connector 17b for connecting a second end of the fluid path set 17 to the at least one syringe 12. In some examples, the fluid path set 17 may have a Y or T configuration and/or other valving (not shown) such that fluid from the first fluid container 19 flows through one portion into the at least one syringe 12 and fluid flows out a second portion from the at least one syringe 12 to the patient.

In some examples, the first syringe 12a may be in fluid communication via the first portion of the fluid path set 17 with a first first fluid container 19a that contains a supply of contrast media agent C or other medical fluid. Similarly, the second syringe 12b may be in fluid communication via the fluid path set 17 with a second first fluid container 19b that contains a supply of saline solution S or other medical fluid. In this manner, the at least two syringes 12a and 12b may be filled with fluid from the at least one first, first fluid container 19a and the at least one second, first fluid container 19b via the fluid path set 17.

Figure 2:
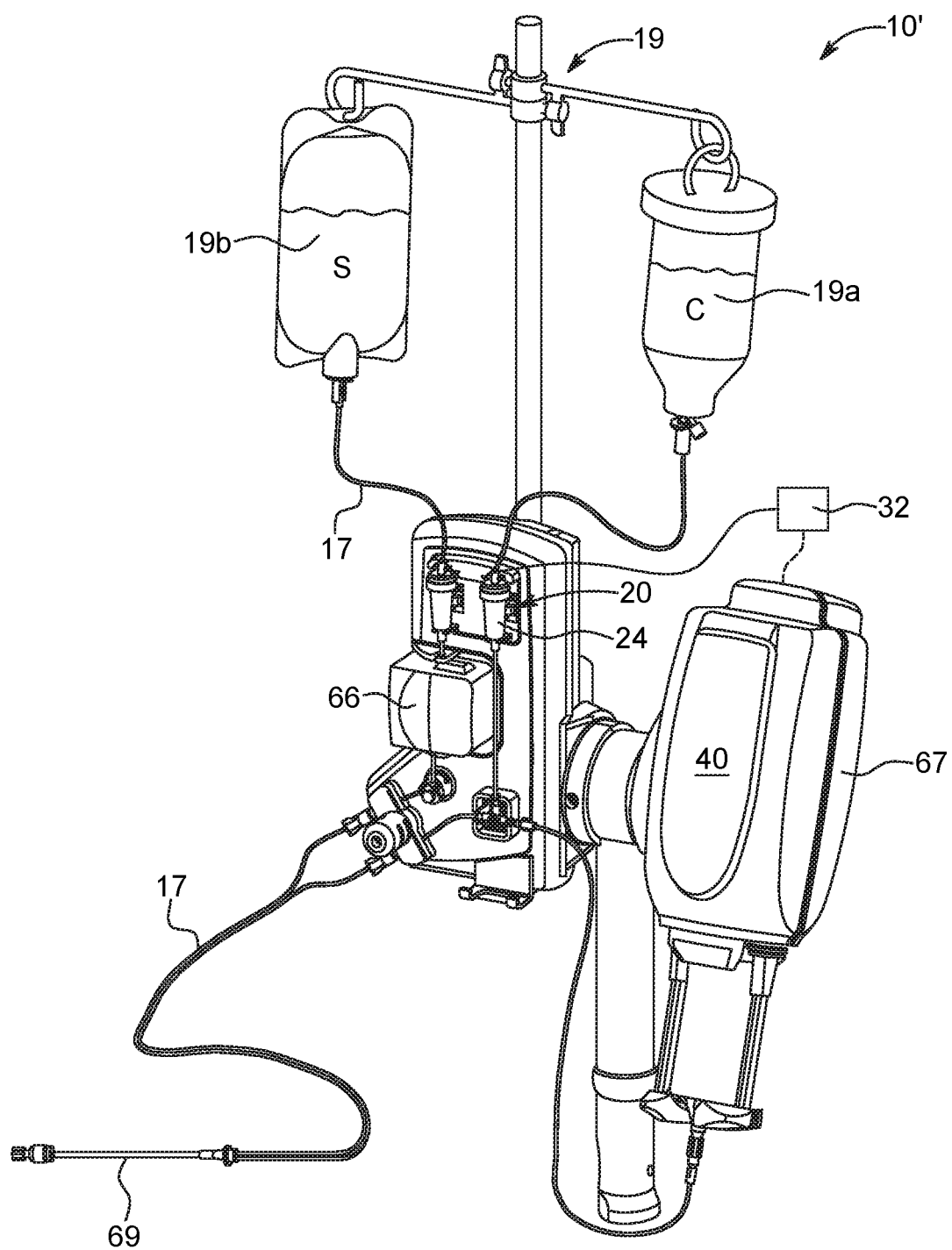
FIG. 2 is a top perspective view of a system including a fluid injector and a heating system according to another aspect of the present disclosure.

With reference to FIG. 2, a fluid injector 10' (hereinafter referred to as "injector 10'") is shown in accordance with another aspect of the present disclosure. The injector 10', such as an automated or powered fluid injector, is adapted to deliver fluid from at least one first fluid container 19, such as the first first fluid container 19a and the second first fluid container 19b, using a pump 66, such as a peristaltic pump, piston pump, or syringe. Each first fluid container 19 may be independently filled with a medical fluid. For example, the first first fluid container 19a may be filled with a first fluid, such as contrast media agent C or any desired medical fluid, while the second first fluid container 19b may be filled with a second fluid, such as saline solution S or any desired medical fluid. The injector 10' may be used during a medical procedure to inject the medical fluid into the body of a patient using the pump 66 and/or a power actuated injector 67. For example, fluid from the first first fluid container 19a may be delivered using the pump 66, while fluid from the second first fluid container 19b may be delivered using the power actuated injector 67. In some examples, fluid from each first fluid container 19 may be delivered using a single pump 66. In other examples, fluid from each first fluid containers 19a, 19b may be delivered using a separate pump 66 or power actuated injector 67. In examples having the pump 66 and the power actuated injector 67, the injector 10' may deliver fluid from one or both of the first fluid containers 19a, 19b simultaneously or sequentially. The at least one fluid path set 17 may be fluidly connected with the at least one first fluid container 19 for delivering the fluid from the at least one first fluid container 19 to a catheter 69 using pump 66.

A heating system 20 may be associated with the injector 10, 10' for heating the fluid from the first fluid container 19. While the heating system 20 may be used with the injector 10 described herein with reference to FIG. 1 or the injector 10' described herein with reference to FIG. 2, the following discussion is focused on describing the use of the heating system 20 in combination with the injector 10 shown in FIG. 1. It is to be understood that the heating system 20 may be used interchangeably with the injector 10' shown in FIG. 2 to heat the fluid in the at least one first fluid container 19, heat the fluid as it is delivered to the second fluid container (e.g., at least one syringe) 12, pump 66, and/or heat the fluid as it is delivered from the pump 66.

With reference to FIG. 1, the heating system 20 may be provided for heating the contrast fluid C as the contrast fluid C is delivered from the first first fluid container 19a to the second fluid container, such as the first syringe 12a, through a first portion of the fluid path set 17. In other examples, the heating system may be provided for heating both the contrast fluid C and the saline S prior to being delivered to the first syringe 12a and the second syringe 12b, respectively. In one non-limiting example, the temperature of the contrast C heated by the heating system 20 may be controlled to be in a range between about 35° C. and about 41° C. In this manner, the heated contrast C can be stored in the first syringe 12a at a temperature approximate to the human body. In some examples, the heating system 20 may be configured to heat the contrast C to a temperature higher than about 41° C. and below a predetermined maximum permissible storage temperature for the contrast C.

With continued reference to FIG. 1, the heating system 20 includes a heater 22 and a fluid path element or cartridge 24. The fluid path element or cartridge 24 may be configured to be in-line with the fluid path set 17 such that fluid that flows from the first fluid container 19 to the at least one syringe 12 also flows through the fluid path element or cartridge 24. In some examples, the fluid path element or cartridge 24 may be removably connected to the fluid path set 17 using one or more connectors 25. For example, the fluid path element or cartridge 24 may have a pair of connectors (one at an inlet and one at an outlet) for connecting with the fluid path set 17 at inlet and outlet sides of the fluid path element or cartridge 24. Alternatively, the fluid path element or cartridge 24 may have a tubing pathway in which the fluid path set 17 may be inserted, for example between opposing surfaces of the fluid path element or cartridge 24, for example wherein the opposing surfaces may be hingedly or otherwise moveable between a first open configuration in which fluid path set 17 may be inserted or removed from the tubing pathway and a second closed configuration in which the fluid path set 17 is maintained between the opposing surfaces of the fluid path element or cartridge 24. In other examples, the first fluid path element or cartridge 24 may be monolithically formed with the fluid path set 17. The fluid path set 17 may be composed of one or more fluid path elements which may be initially separate or come pre-connected for use. In certain embodiments, the fluid path element or cartridge 24 may be an example of a fluid path element. For example, the fluid path element or cartridge 24 may be the fluid path element which can be engage with or otherwise inserted into the heater 22 or the at least one heating element 28.

The heater 22 may have at least one heating element 28 configured for raising the temperature of the fluid flowing through the fluid path element or cartridge 24. In some examples, two or more heating elements 28 may be provided such that the fluid path element or cartridge 24 may be disposed between the pair of heating elements 28 such as opposing heating element s 28 in a clamshell configuration. In some examples, at least a portion of the heater 22, such as the portion that contacts the fluid path element or cartridge 24 may be made from a material that conforms to the exterior shape of the fluid path element or cartridge 24 or alternatively the portion of the fluid path element or cartridge 24 may be made from a material that conforms to the interior shape of the heater 22. In this manner, when the fluid path element or cartridge 24 is connected to the heater 22, the one or more heating elements 28 may be in thermal transfer contact, for example direct physical contact with the fluid conduit 26 of the fluid path element or cartridge 24. In other examples, the one or more heating elements 28 may be in indirect thermal transfer contact, for example by indirect physical contact with the fluid conduit 26 of the fluid path element or cartridge 24 wherein thermal energy is transferred by microwaves, infrared radiation, or other radiative or convective means of heat transfer that do not require direct physical contact. The at least one heating element 28 may transfer heat to the fluid within the fluid path element or cartridge 24 by conduction, convention, radiation, or any combination thereof. The at least one heating element 28 may use electrical, mechanical, radiative, or chemical energy as a source for heating the fluid flowing through the at least one fluid conduit 26. For example, the at least one heating element 28 may have at least one plate made from a highly conductive metal or silicon rubber in thermal contact with at least a portion of the fluid path element or cartridge 24. In various examples, thermal energy from the at least one heating element 28 may be transferred to the fluid flowing through the fluid path element or cartridge 24 by ultrasonic means, microwave energy means, inductive energy means, friction, infrared radiation transfer, convective energy transfer, conductive energy transfer, any other electrical, mechanical, radiative, or chemical means, or any combination thereof. In use, the at least one heating element 28 may be used to directly heat the fluid flowing through the at least one fluid conduit 26, and/or heat the at least one fluid conduit 26, which heats the fluid through thermal contact with the fluid. A plurality of heating elements 28 may be provided in parallel and/or series to heat the fluid in one or more stages as the fluid flows through the fluid path element or cartridge 24.

Figure 3:
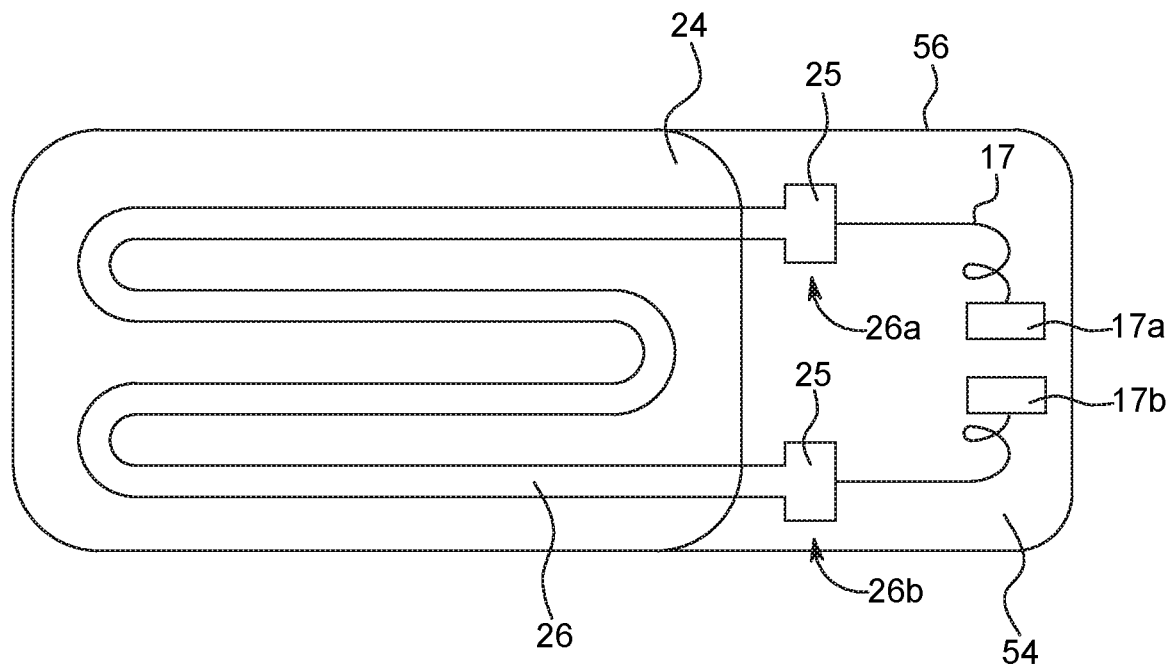
FIG. 3 is a top view of a cartridge for use with the contrast heating system shown in FIG. 1.

With reference to FIG. 3, the fluid path element or cartridge 24 may have at least one fluid conduit 26 through which fluid flows as it is delivered from the first fluid container 19 to the at least one second fluid container, such as syringe 12. The at least one fluid conduit 26 may have a serpentine path to increase a surface area over which the at least one fluid conduit 26 contacts the at least one heating element 28 and maximize exposure of the fluid flowing through the at least one fluid conduit 26 to the thermal energy from the at least one heating element 28. A first end 26a of the fluid conduit 26 may be configured for fluid connection with the at least one first fluid container 19 via a first portion of the fluid path set 17 having the first connector 17a, while the second end 26b of the fluid conduit 26 may be configured for fluid connection with the second fluid container 12, for example the at least one syringe 12 via a second portion of the fluid path set 17 via the second connector 17b. The fluid path element or cartridge 24 may have a housing 54 having a storage compartment 56 for storing tubing of the fluid path set 17 prior to use. The storage compartment 56 may have a removable lid (not shown) that encloses the fluid path set 17. In some examples, the fluid path element or cartridge 24 may be constructed from a medical-grade plastic material. The fluid conduit 26 of the fluid path element or cartridge 24 may be sufficiently rigid to prevent collapsing when filling and heating under vacuum conditions.

Figure 4:
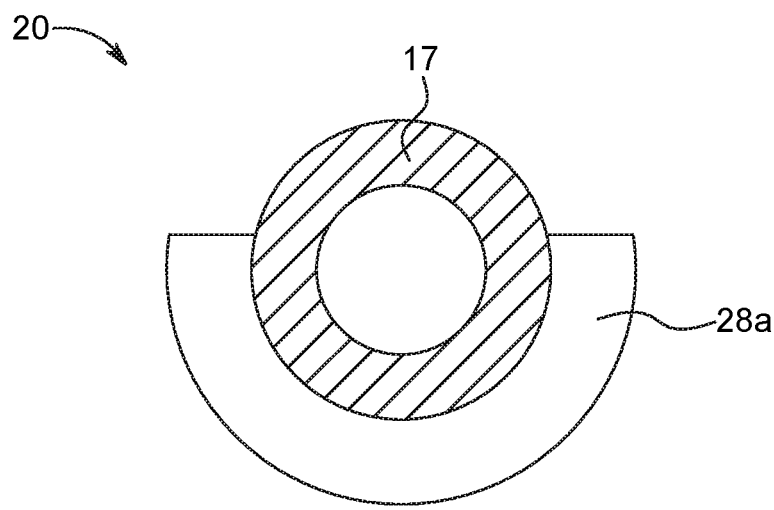
FIG. 4 is a cross-sectional view of a heating system according to another aspect of the present disclosure.

With reference to FIG. 4, the heating system 20 may directly heat the fluid flowing through the fluid path set 17 without the need for the fluid path element or cartridge 24. For example, the heating system 20 may be configured as a sleeve 28a that at least partially envelops the fluid path set 17 along at least a portion of the longitudinal length of the fluid path set 17 between the at least one first fluid container 19 and the at least one second fluid container 12. The sleeve 28a may be removably or non-removably connected to the fluid path set 17. In various examples, thermal energy from the sleeve 28a may be transferred to the fluid flowing through the fluid path set 17 by ultrasonic means, microwave energy means, inductive energy means, friction, infrared radiation transfer, convective energy transfer, conductive energy transfer, any other electrical, mechanical, radiative, or chemical means, or any combination thereof.

Figure 5A:
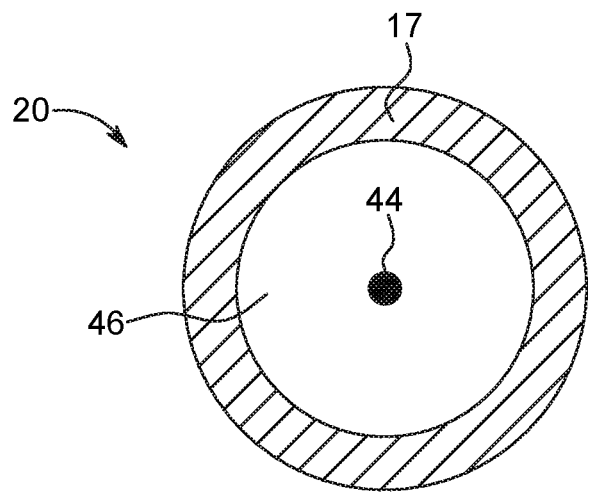
FIGS. 5A-5B are cross-sectional views of a heating system according to another aspect of the present disclosure.
Figure 5B:
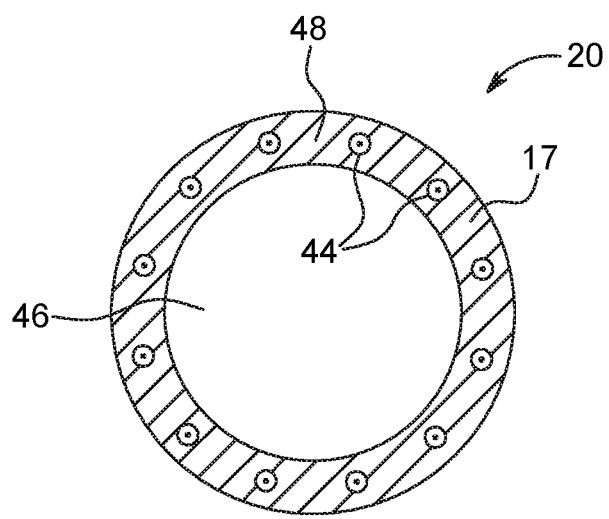

With reference to FIGS. 5A-5B, the heating system 20 may be positioned within the fluid path set 17. For example, the heating system 20 may have one or more heated wires 44 extending through a central lumen 46 of the fluid path set 17 (FIG. 5A). Alternatively, or in addition, the heating system 20 may have one or more heated wires 44 at least partially embedded within the sidewall 48 of the fluid path set 17 (FIG. 5B). The one or more heated wires 44 may extend over at least a portion of the longitudinal length of the fluid path set 17 between the at least one first fluid container 19 and the at least one syringe 12. In some examples, the one or more heated wires 44 may be made from copper, stainless steel, or other suitable resistive material.

Figure 6A:
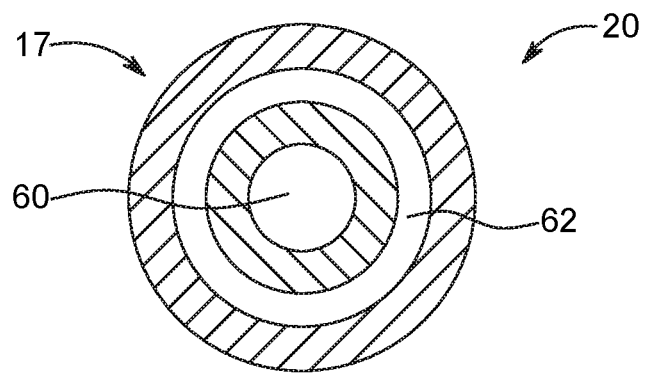
FIGS. 6A-6C are cross-sectional views of a heating system according to another aspect of the present disclosure.
Figure 6B:
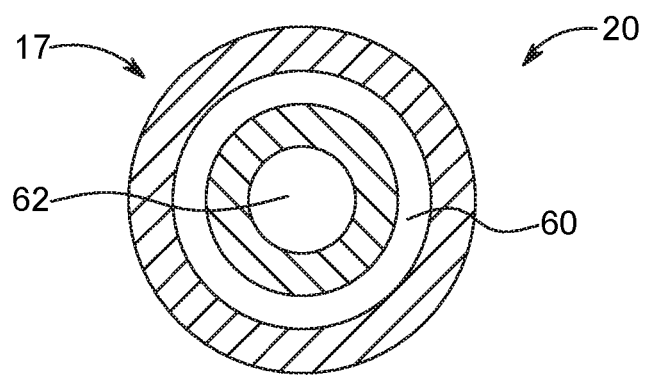
Figure 6C:
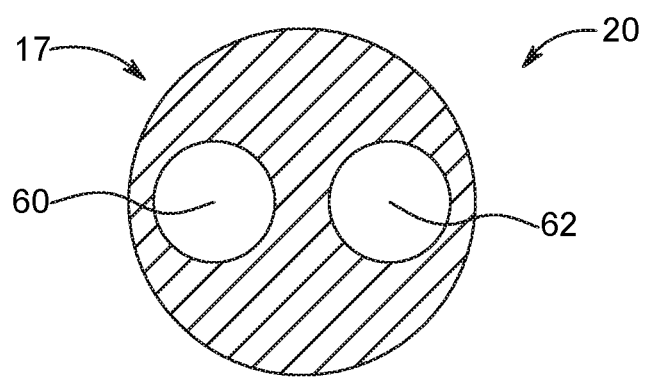

With reference to FIGS. 6A-6C, the heating system 20 may be combined with the fluid path set 17 that has a multi-lumen configuration with at least one first lumen 60 for delivering the fluid from the at least one first fluid container 19 to the at least one at least one second fluid container 12 and at least one second lumen 62 for receiving a warming fluid heated by a heat source (not shown). The at least one first lumen 60 and the at least one second lumen 62 may be in thermal contact with one another such that thermal energy from the warming fluid may be transferred to the fluid flowing through the at least one first lumen 60 as the fluid is delivered from the at least one first fluid container 19 to the at least one second fluid container 12. The at least one first lumen 60 and the at least one second lumen 62 may be coaxial such that the at least one first lumen 60 is positioned within an interior of the at least one second lumen 62 and extends coaxially therewith (FIG. 6A). Alternatively, the at least one second lumen 62 may be positioned within an interior of the at least one first lumen 60 and may extend coaxially therewith (FIG. 6B). In other examples, the at least one first lumen 60 and the at least one second lumen 62 may be parallel to one another and offset radially from one another (FIG. 6C) for example in a helical orientation or with one lumen wrapped around the other lumen. The at least one second lumen 62 is configured for flowing a warming fluid, such as heated liquid or gas in the same or opposite direction of flow of the at least one first lumen 60. The at least one second lumen 62 may extend over at least a portion of the longitudinal length of the fluid path set 17 between the at least one first fluid container 19 and the at least one second fluid container 12.

Figure 7:
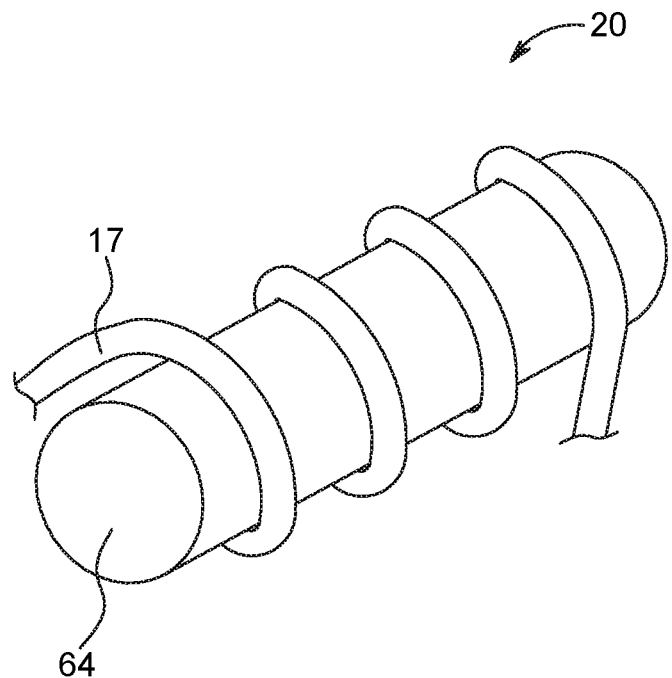
FIG. 7 is a perspective view of a heating system according to another aspect of the present disclosure.

With reference to FIG. 7, the heating system 20 may have a heating core 64 around which at least a portion of the fluid path set 17 is wrapped in a helical or spiral arrangement. Desirably, the helical or spiral fluid path set 17 may be in thermal contact with the heating core 64 such that thermal energy from the heating core 64 is transferred to the fluid flowing through the fluid path set 17. The heating core 64 may be heated by passing heated gas or liquid through an interior of the heating core 64 to heat an exterior surface of the heating core 64. In some examples, the heating core 64 may have one or more heating elements (not shown) for heating the exterior surface of the heating core 64 or for heating the heated gas or liquid flowing through the interior of the heating core 64. The heating core 64 may extend over at least a portion of the longitudinal length of the fluid path set 17 between the at least one first fluid container 19 and the at least one second fluid container 12.

Figure 8:
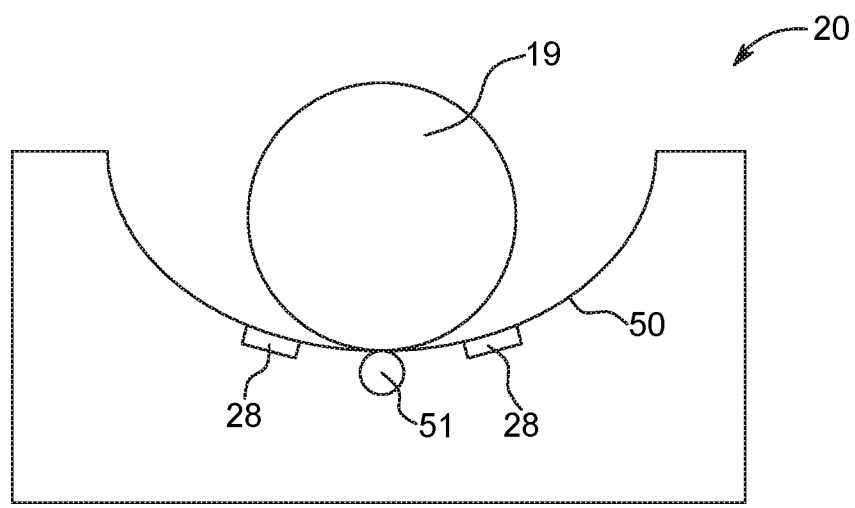
FIG. 8 is a side view of a heating system according to another aspect of the present disclosure.

With reference to FIG. 8, the heating system 20 may be configured for heating at least a portion of a single instance of the at least one first fluid container 19 before or upon connection to the fluid path set 17. For example, the heating system 20 may have a heating interface 50 having a concave shape configured for receiving at least a portion of the sidewall of the at least one first fluid container 19. In some examples, a diameter of the heating interface 50 is larger than a diameter of the at least one first fluid container 19 such that at least a portion of the first fluid container 19 can be received within the heating interface 50. The heating interface 50 optionally may have a rolling mechanism 51 configured for contacting the sidewall of the at least one first fluid container 19 and rotating the at least one first fluid container 19 about its longitudinal axis 52, for example to ensure substantially even heating of the fluid in the at least one first fluid container 19. The rolling mechanism 51 may have a rubber contact surface for preventing slipping at the interface between one or more rotating wheels of the rolling interface 50 and an outer surface of the at least one first fluid container 19. The heating system 20 may have one or more heating elements 28 in thermal contact with the heating interface 50 to transfer heat energy to the fluid in the at least one first fluid container 19. In various examples, thermal energy from the heating interface 50 may be transferred to the fluid in the at least one first fluid container 19 by ultrasonic means, microwave energy means, inductive energy means, friction, infrared radiation transfer, convective energy transfer, conductive energy transfer, any other electrical or chemical means, or a combination thereof. A benefit of this embodiment of heating system 20 is that its operation is integrated into the injector and data about the presence, timing or activities, and/or temperature of the first container 19 or fluid therein may be sensed, transmitted, recorded, and/or utilized by the controller 32, as discussed elsewhere herein.

Figure 9:
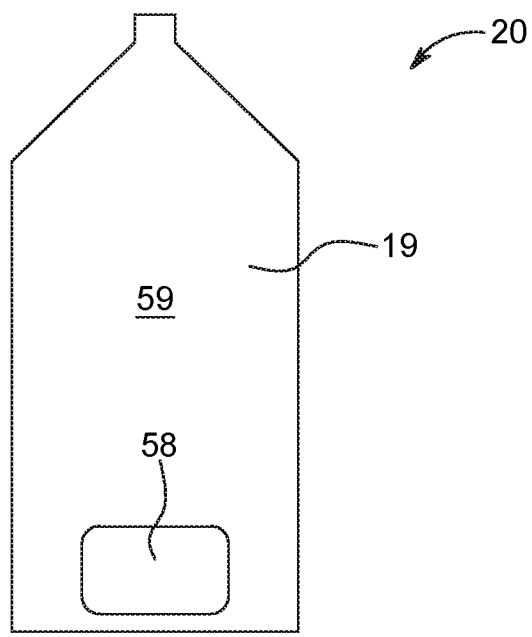
FIG. 9 is a front view of a heating system according to another aspect of the present disclosure.

With reference to FIG. 9, the heating system 20 may have a heat packet 58 in thermal contact with the interior 59 of the at least one first fluid container 19. The heat packet 58 may be activated from an initial, unheated state to a final, heated state by, for example, shaking the at least one first fluid container 19. By undergoing an exothermic chemical reaction or physical process (such as crystallization) between the initial and final states, the heat packet 58 releases thermal energy which is absorbed by the fluid within the at least one first fluid container 18, thereby raising the temperature of the fluid.

Figure 10:
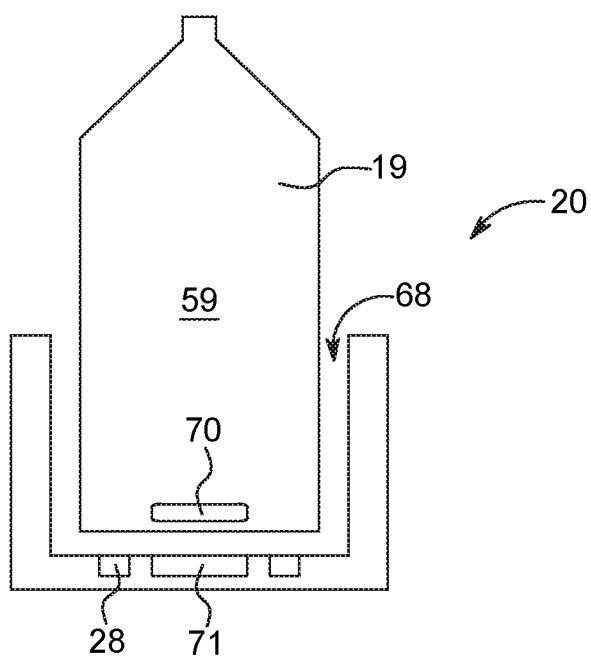
FIG. 10 is a cross-sectional view of a heating system according to another aspect of the present disclosure.

With reference to FIG. 10, at least a portion of the at least one first fluid container 19 may be disposed within the heating system 20. For example, the heating system 20 may have a receiving space 68 for receiving at least a portion of the at least one first fluid container 19. The at least a portion of the at least one first fluid container 19 that is received within the receiving space 68 may be in thermal contact with a heating element 28, or other heat source, to heat the fluid within the at least one first fluid container 19. In some examples, the at least one first fluid container 19 may be immersed in a heated liquid or steam filling at least a portion of the receiving space 68. In other examples, the at least one first fluid container 19 may have a metallic stirring element 70, for example a magnetic stir-bar that is rotated by a magnetic stirrer 71 to stir the fluid and ensure even heating the fluid in the at least one first fluid container 19. In other examples, thermal energy from within the receiving space 68 may be transferred to the fluid in the at least one first fluid container 19 by ultrasonic means, microwave energy means, inductive energy means, friction, infrared radiation transfer, convective energy transfer, conductive energy transfer, any other electrical or chemical means, or any combination thereof.

Figure 11:
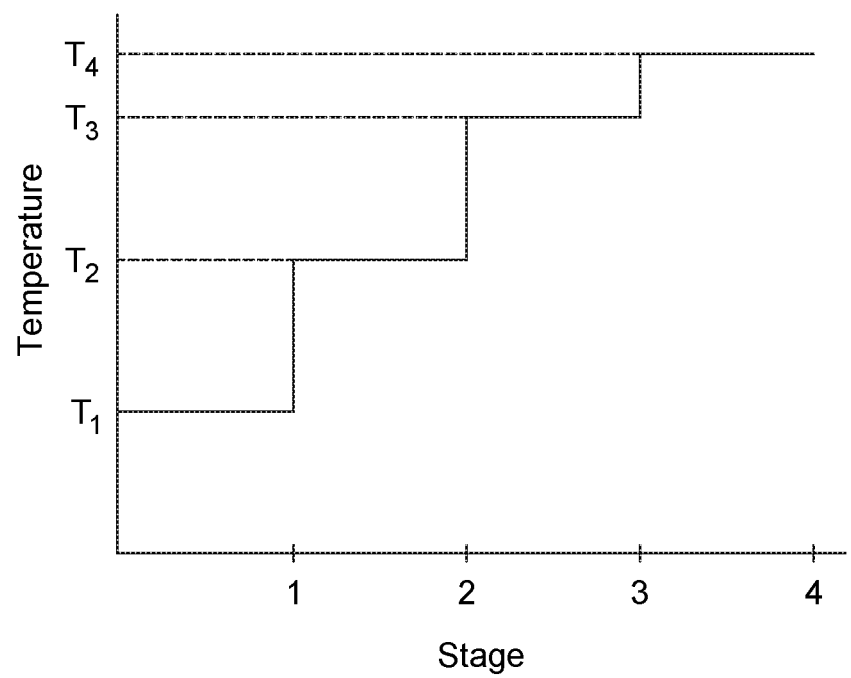
FIG. 11 is a graph of a multi-stage heating system according to another aspect of the present disclosure.

With reference to FIG. 11, the fluid from the at least one first storage container 19 may be heated in a plurality of stages prior to being delivered to the patient using the injector 10 or 10'. At each stage the temperature of the fluid may be incrementally increased from the previous stage such that the temperature of the fluid at the final stage is within a desired temperature range. For example, the at least one first fluid container 19 may initially be stored at a first temperature $T_1$. The first temperature $T_1$ may be a temperature suitable for long-term storage of the fluid within the at least one first fluid container 19. Prior to use, the at least one first fluid container 19 may optionally be moved to a warming oven which raises the temperature of the fluid within the at least one first fluid container 19 to a second temperature $T_2$ that is higher than the first temperature $T_1$. When the at least one first fluid container 19 is ready for use, it may be connected to the injector 10, 10' such that the heating system 20 raises the temperature of the fluid within the at least one first fluid container 19 to a third temperature $T_3$ that is higher than the second temperature $T_2$. In some examples, the temperature of the fluid within the at least one first fluid container 19 may be raised to a fourth temperature $T_4$, which is higher than a third temperature $T_3$. The fourth temperature $T_4$ may be within a desired temperature range for delivering the fluid to the patient using the injector 10, 10'. One or more additional stages of warming may be provided to gradually increase the temperature of the fluid from a first temperature $T_1$ to a final temperature within a desired temperature range for delivering the fluid to the patient using the injector 10, 10'. Benefits of such sequential heating may include the ability to reduce the amount of energy needed at any single stage of heating and a reduction in the likelihood of overheating or an overshoot on the temperature. It is desirable to avoid an over temperature condition as it may harm the patient.

In some examples, fluid from the at least one first fluid container 19 may be heated due to shear forces on the fluid as it passes through at least a portion of the fluid path set 17. For example, the injector 10, 10' may be used to repeatedly fill the at least one second fluid container 12 with fluid from the at least one first fluid container 19 and empty the at least one second fluid container 12 by delivering the fluid back into the at least one first fluid container 19. As the fluid is delivered under pressure through the fluid path set 17 from the at least one second fluid container 12 to the at least one first fluid container 19, the temperature of the fluid may be increased due to the shear stresses on the fluid in the fluid path set 17. The temperature of the fluid can be increased incrementally with each transfer of the fluid from the at least one first fluid container and the at least one second fluid container 12 until the temperature is within a desired temperature range. Alternatively, once an intermediate temperature is reached by shear force heating, the fluid may be heated the rest of the way to the desired final temperature by any of the heating methods described herein.

In other examples, fluid can be cycled under pressure through tubing between two second fluid containers, for example two syringes 12a, 12b. The temperature of the fluid can be increased incrementally with each filling and emptying cycle between the two syringes 12a, 12b until the temperature of the fluid is within a desired temperature range.

Figure 12A:
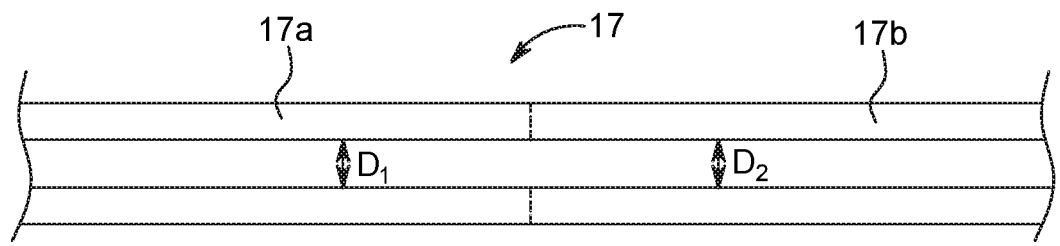
FIGS. 12A-12B are cross-sectional views of a heating system according to another aspect of the present disclosure.
Figure 12B:
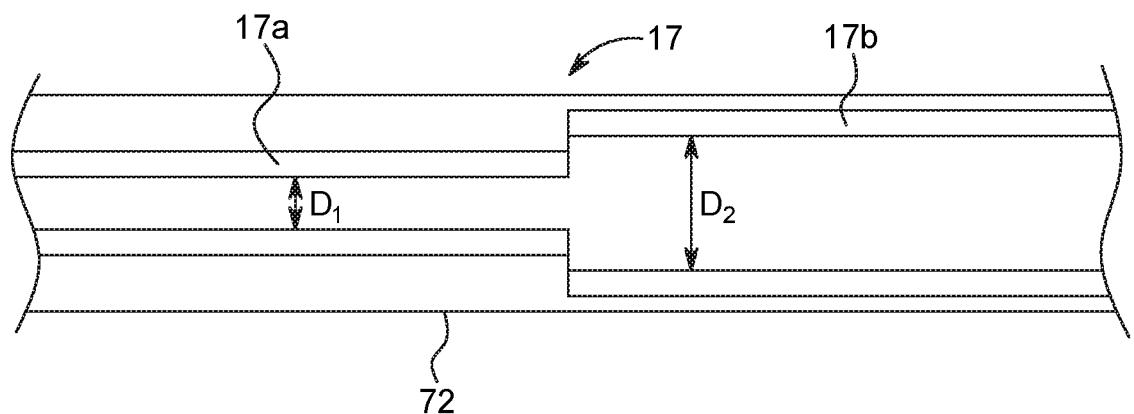

In other examples, fluid from the at least one first fluid container 19 may be heated due to a pressure drop within the tubing of the fluid path set 17. For example, a restriction in the tubing of the fluid path set 17 may be configured to cause a pressure drop between a portion of the fluid path set 17 upstream of the restriction and a portion of the fluid path set 17 downstream of the restriction. Alternatively, with reference to FIGS. 12A, 12B, a first portion 17a of the fluid path set 17 may be made from a first material, while a second portion 17b of the fluid path set 17 may be made form a second material different from the first material. The second material may be more flexible than the first material, thereby allowing the second portion 17b to expand during a pressurized delivery of the fluid through the fluid path set 17. In some examples, the second portion 17b of the fluid path set 17 may expand to have a larger inner diameter, such as by a factor of two, when pressurized at a typical injection pressure than when not under pressure (see FIGS. 12A, 12B). The pressure drop between the first portion 17a and the second portion 17b may cause an increase in the temperature of the fluid flowing through the fluid path set 17. At least a portion of the fluid path set 17, such as the second portion 17b, may have a sleeve 72 to limit the radial expansion of the sidewall of the fluid path set 17 under pressure.

In some examples, the injector 10 may have a heat maintainer 29 (shown in FIG. 1) for maintaining the temperature of the heated fluid, for example contrast C. In some examples, the heat maintainer 29 may be configured for heating the fluid within the at least one second fluid container 12 without the need for preheating using the heater 22. For example, the heat maintainer 29 may be configured as a sleeve surrounding at least a portion of the at least one syringe 12. In other embodiments, the heat maintainer 29 may maintain the temperature of the heated contrast C to prevent a drop in temperature if the contrast C is not injected shortly after being heated by the heater 22. Alternatively, the heat maintainer 29 may raise the temperature of unheated contrast C prior to injecting the contrast C into the patient. In some examples, the heat maintainer 29 may have a timer that turns off the heat maintainer 29 after a predetermined period of time. In some examples, the heat maintainer 29 may have a thermostat to limit the temperature rise and to optionally provide information on the fluid temperature to the system and/or the user. In various examples, thermal energy from the heat maintainer 29 may be transferred to the fluid within the at least one syringe 12 by ultrasonic means, microwave energy means, inductive energy means, friction, infrared radiation transfer, convective energy transfer, conductive energy transfer, any other electrical or chemical means, or any combination thereof. In some examples, the heat maintainer 29 may be used with the first fluid container 19 instead of, or in addition to, use with the at least second fluid container, for example syringe 12. The at least one second fluid container 12 and/or the at least one first fluid container 19 may have a thermally-conductive coating that improves transfer of thermal energy to the fluid in the at least one second fluid container 12 and/or the at least one first fluid container 19.

Figure 13:
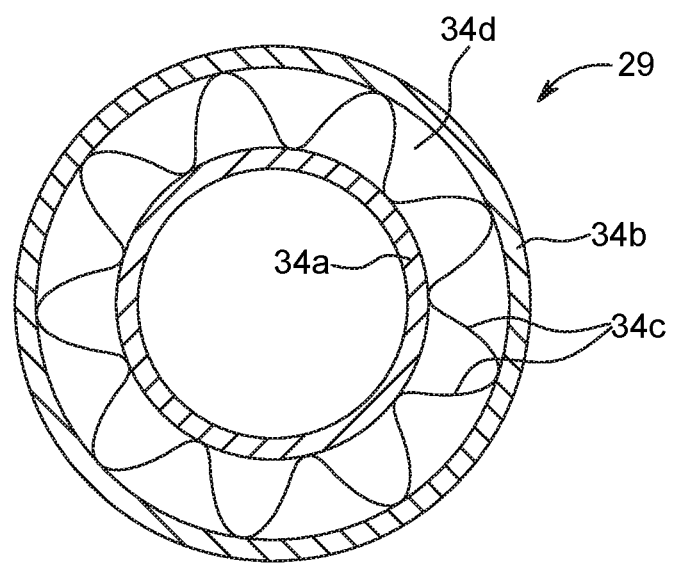
FIG. 13 is a cross-sectional view of a heat maintainer according to another aspect of the present disclosure.

With reference to FIG. 13, the heat maintainer 29 may have an inner sleeve 34a, an outer sleeve 34b surrounding the inner sleeve 34a, and one or more fins 34c connecting the inner sleeve 34a with the outer sleeve 34b. A space 34d between the fins 34c may be filled with heated liquid or gas, thermal energy of which is transferred to the at least one second fluid container 12 disposed within the inner sleeve 34a. In other examples, the heat maintainer 29 may be a heat lamp (not shown) positioned to direct thermal energy to the at least one second fluid container 12.

Figure 14:
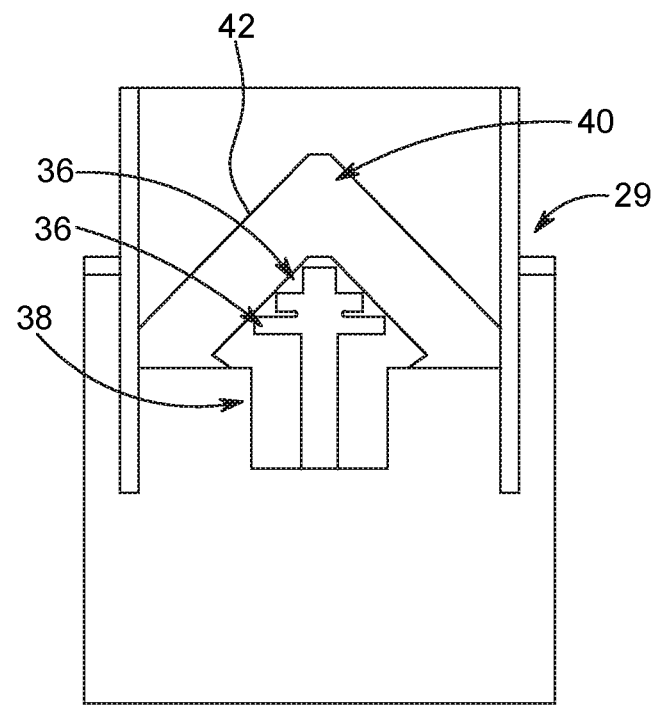
FIG. 14 is a cross-sectional view of a heat maintainer according to another aspect of the present disclosure.

With reference to FIG. 14, the heat maintainer 29 may have at least one heating element 36 positioned in a piston 38 of the fluid injector 10. According to this embodiment, the at least one heating element 36 may be in thermal contact with a plunger 40 of the at least one syringe 12 when the piston 38 is connected with the plunger 40 to reciprocally drive the plunger 40 through the barrel of the at least one syringe 12. Heat transferred to the plunger 40 from the at least one heating element 36 in the piston 38 is in turn transferred to the fluid within the at least one syringe 12. In some examples, the at least one heating element 36 may have one or more heating bands in a distal tip portion 42 of the piston 38.

The heating system 20 may have at least one sensor, for example at least one temperature sensor 30 for measuring the temperature of the fluid. In some examples, the at least one temperature sensor 30 may be positioned at an inlet of the at least one fluid conduit 26, an outlet of the at least one fluid conduit 26, and/or any location between the inlet and the outlet of the at least one fluid conduit 26. Alternatively, or in addition, at least one temperature sensor 30 may be configured for measuring the temperature of fluid within at least one of the syringes 12a, 12b and/or at least one of the first fluid containers 19a, 19b, or any part of fluid path 17. In various examples, the at least one temperature sensor 30 may be a contact thermometer, an infrared thermometer, a phase change indicator, or a combination thereof. Alternatively, the at least one sensor may be a flow sensor which may determine the temperature of the fluid based on flow rate, tubing diameter, and fluid viscosity values.

Figure 15:
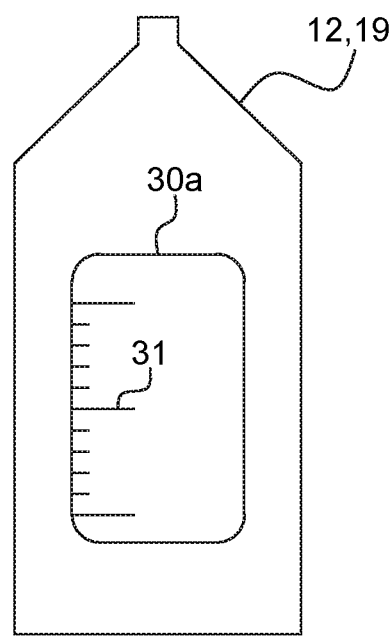
FIG. 15 is a side view of a temperature sensor according to another aspect of the present disclosure.

With reference to FIG. 15, the at least one temperature sensor 30 may be a thermochromic ink label or other marking 30a applied to at least a portion of the at least one second fluid container 12 and/or the at least a portion of the at least one first fluid container 19. For example, the label 30a may be applied to a surface of the at least one second fluid container 12 or first fluid container 19, such as an external surface of the at least one syringe 12 or contrast bottle 19. The label 30a may change color based on the temperature of the contents of the at least one first and/or second fluid container, 19 and/or 12 respectively. In some examples, the label 30a may have indicia 31 that indicate a temperature of the contents of the at least one first and/or second fluid container 19, 12 based on the color of the thermochromic ink of the label 30a. In some examples, the label 30a may contain information regarding the contents of the at least one second fluid container 12 or the at least one first fluid container 19. The label 30a may be read by a user of the injector to determine the temperature of the contrast fluid prior to initiating an injection protocol; or alternatively may be read by an injector controller 32, for example by image recognition using a camera, to determine the temperature of the contrast prior to initiating an injection protocol.

Various heating systems 20 described herein may be controlled by a controller 32 (shown in FIG. 1). In various examples, the controller 32 may be configured to control the operation of the heating system 20, such as selectively turning on or off or varying the power to the at least one element 28 or other heating means based on temperature readings of the at least one temperature sensor 30. The controller 32 may have or receive and utilizes information about the heating system 20, for example its wattage, heat capacity, and/or heat transfer resistance to properly control the heating system 20. The information about the heating system 20 may be communicated in digital, analog, or other form or may be incorporated into the controller 32. The controller 32 may receive temperature data from the at least one temperature sensor 30, for example by wired or wireless connection, and transmit the temperature data to the fluid injector 10, 10' via a wired or wireless connection. A first example of a control algorithm may be used by the controller 32 may include increasing or decreasing the power to the heating system 20 proportional to the fluid flow rate multiplied by the temperature difference between the inlet fluid temperature and the desired fluid temperature. A second example of a control algorithm may use the values for the selected fill volume and initial fluid temperature to provide a fixed amount of energy to the heating system 20 to heat the fluid(s) as it flows through the fluid path 17. A third example of a control algorithm may maintain the heater at the desired target temperature and may include information that the heat capacity of the heater is sufficient such that the fluid flowing through it will be heated to the desired temperature without significantly decreasing the temperature of the heating system 20. A combination of these and other control algorithms may be used. The controller 32 may be provided as a standalone unit, be incorporated into the heating system 20, or be incorporated into the fluid injector 10, 10'. The controller 32 may incorporate information about the temperature, viscosity, and/or rate of fluid flow through the at least one fluid conduit 26 to adjust the amount of energy provided to the at least one heating element 28 based on the flow rate through the at least one fluid conduit 26. This may be done in anticipation of fluid flow through the at least one fluid conduit 26, for example, just before or during the initial phases of fluid flow through the at least one fluid conduit 26 to ensure that the fluid is fully heated. For example, the controller 32 may provide an amount of energy to the at least one heating element 28 that calculates the contact time of the fluid as it flows through the at least one fluid conduit 26 or fluid path 17, so that it heats the at least one heating element 28 to a temperature that provides the desired final temperature of the fluid. In one example where fluid contact time is short, the controller 32 may heat the at least one heating element 28 to a temperature significantly higher than the desired final fluid temperature so that the combination of high heating element temperature and short contact time provides a desired final temperature to the fluid.

The fluid injector 10, 10' may be configured or programmed to recall one or more pre-programmed injection protocols or to modify one or more selected pre-programmed injection protocols based on temperature data received from the controller 32 and desired final temperature of the fluid. For example, the fluid injector 10, 10' may adjust the injection pressure limit, such as by raising or lowering the pressure limit, for the fluid path set 17 based on the temperature of the fluid. In this manner, the pressure limit for a pre-programmed injection protocol may be raised to compensate for the reduced viscosity of heated contrast.

The heating system 20 may be connected to a display 40 on the fluid injector 10, 10' and/or the heater 22 operative to present a user interface, such as a graphical user interface (GUI), for accessing information and to perform functions associated with the heating system 20. The GUI may provide information and functions associated with the heating system 20. For example, the GUI interface may provide temperature information of the fluid flowing through the fluid path element or cartridge 24, or the fluid in at least one of the second fluid containers, such as syringes 12. In another example, the GUI interface may provide functions for adjusting the temperature, and turning the heating elements 28 on or off. In one example, the display 40 may be a touch sensitive display including virtual keys and buttons for data entry, such as alphanumeric keys and symbolic keys. One or more parameters relating to the heating system 20, such as the temperature of the contrast C, may be stored in a database for later retrieval or transferred to a network, such as a hospital information network, and associated with a particular injection procedure.

The heating system 20 may be connected to one or more networks and/or one or more electronic devices through one or more communication ports according to known communication methods. Illustrative and non-limiting examples of communication methods available through the communication ports include Ethernet, wireless protocols (e.g., Wi-hi 802.11g, 802.11n, etc.), serial, universal serial bus (USB), parallel port, Bluetooth®, and proprietary device protocols for barcode reader, RFID readers, QR code readers, temperature sensors, etc.).

Although the disclosure has been described in detail for the purpose of illustration based on what are currently considered to be the most practical and preferred examples, it is to be understood that such detail is solely for that purpose and that the disclosure is not limited to the disclosed examples, but, on the contrary, is intended to cover modifications and equivalent arrangements. For example, it is to be understood that the present disclosure contemplates that, to the extent possible, one or more features of any example can be combined with one or more features of any other example.

We claim:

1. A system for heating a medical fluid, the system comprising:
    at least one first fluid container for storing a fluid;
    a fluid injector having at least one second fluid container for receiving the fluid from the at least one first fluid container through a fluid path set;
    at least one fluid path element positioned in-line with at least a segment of the fluid path set between the at least one first fluid container and the at least one second fluid container of the fluid injector, wherein the at least one fluid path element is configured to heat the fluid to a pre-determined temperature as the fluid flows through the at least one fluid path element;
    a controller for controlling an output of the at least one fluid path element based on at least one of a property of the at least one fluid path element and a property of the fluid flowing through the at least one fluid path element; and
    at least one temperature sensor configured for measuring a temperature of the fluid flowing through at least a portion of the at least one fluid path element,
    wherein the controller is configured to receive temperature data from the at least one temperature sensor and transmit the temperature data to the fluid injector via a wired or wireless connection, and
    wherein the fluid injector is configured to adjust a pre-programmed maximum injection pressure limit of a pre-programmed injection protocol based in part on the temperature of the fluid.

2. The system of claim 1, wherein the at least one fluid path element has at least one fluid conduit having a first end in fluid communication with a first portion of the fluid path set connected to the first fluid container and a second end in fluid communication with a second portion of the fluid path set connected to the at least one second fluid container.

3. The system of claim 2, wherein the at least one fluid conduit of the at least one fluid path element has a serpentine path.

4. The system of claim 1, wherein the at least one fluid path element is removably connected to the fluid path set with one or more connectors or by placing the fluid path set within a tubing pathway of the fluid path element.

5. The system of claim 1, wherein the at least one fluid path element is monolithically formed with the fluid path set.

6. The system of claim 1, wherein the at least one fluid path element comprises a pair of heating elements provided on opposing sides of the at least one fluid path element.

7. The system of claim 1, wherein the at least one fluid path element comprises a plurality of heating elements arranged in series along a longitudinal length of the at least one fluid path element.

8. The system of claim 1, wherein the at least one fluid path element comprises a plurality of heating elements arranged in parallel along a length of the at least one fluid path element.

9. The system of claim 1, wherein the at least one temperature sensor is positioned at at least one of an inlet of at least one fluid conduit of the at least one fluid path element, an outlet of the at least one fluid conduit of the at least one fluid path element, and a location between the inlet and the outlet of the at least one fluid conduit of the at least one fluid path element.

10. The system of claim 1, wherein the at least one temperature sensor is a contact thermometer, an infrared thermometer, a thermochromic ink label or marking, a phase change indicator or combination of any thereof.

11. The system of claim 1, further comprising a heat maintainer associated with the at least one second fluid container for maintaining a temperature of the fluid at the pre-determined temperature.

12. The system of claim 11, wherein the heat maintainer comprises a sleeve surrounding at least a portion of the at least one second fluid container.

13. A system for heating a medical fluid, the system comprising:
    at least one first fluid container for storing a fluid;
    a fluid injector having at least one pump for delivering the fluid from the at least one first fluid container to a patient through a fluid path set;
    at least one fluid path element positioned between the at least one first fluid container and the at least one pump of the fluid injector for heating the fluid to a pre-determined temperature;
    a controller for controlling an output of the at least one fluid path element based on at least one of a property of the at least one fluid path element and a property of the fluid flowing through the fluid path set; and
    at least one temperature sensor configured for measuring a temperature of the fluid flowing through at least a portion of the at least one fluid path element,
    wherein the controller is configured to receive temperature data from the at least one temperature sensor and transmit the temperature data to the fluid injector via a wired or wireless connection, and
    wherein the fluid injector is configured to adjust a pre-programmed maximum injection pressure limit of a pre-programmed injection protocol based in part on the temperature of the fluid.

14. The system of claim 13, wherein the at least one pump comprises a peristaltic pump or a syringe.

15. The system of claim 13, wherein the at least one temperature sensor is positioned at at least one of an inlet of the fluid path set, an outlet of the fluid path set, and a location between the inlet and the outlet of the fluid path set.

* * * * *

UNITED STATES PATENT AND TRADEMARK OFFICE
CERTIFICATE OF CORRECTION

PATENT NO. : 11,013,857 B2  
APPLICATION NO. : 16/314897  
DATED : May 25, 2021  
INVENTOR(S) : Uber, III et al.

Page 1 of 1

It is certified that error appears in the above-identified patent and that said Letters Patent is hereby corrected as shown below:

In the Specification
In Column 12, Line 24, delete "first fluid container 18," and insert -- first fluid container 19, --, therefor.
In Column 13, Line 53, delete "form" and insert -- from --, therefor.
In Column 16, Line 56, delete "Wi-hi" and insert -- Wi-Fi --, therefor.
In Column 16, Line 59, delete "for" and insert -- (e.g., for --, therefor.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*